United States Patent
Baic et al.

(10) Patent No.: US 12,251,576 B2
(45) Date of Patent: Mar. 18, 2025

(54) ELECTROMAGNETIC INTERFACE MOUNT FOR RADIATION MACHINES

(71) Applicant: Varian Medical Systems, Inc., Palo Alto, CA (US)

(72) Inventors: Dusan Baic, Santa Clara, CA (US); Veselin Kolev, Redwood City, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 1063 days.

(21) Appl. No.: 17/038,657

(22) Filed: Sep. 30, 2020

(65) Prior Publication Data
US 2022/0096866 A1   Mar. 31, 2022

(51) Int. Cl.
*A61N 5/10* (2006.01)
*A61N 5/06* (2006.01)

(52) U.S. Cl.
CPC .... *A61N 5/1048* (2013.01); *A61N 2005/0632* (2013.01); *A61N 2005/0651* (2013.01); *A61N 2005/1074* (2013.01)

(58) Field of Classification Search
CPC .......... A61N 5/1048; A61N 2005/0632; A61N 2005/0651; A61N 2005/1074; B60R 2011/0057; B60R 2011/007
USPC ............ 248/206.5, 683, 537, 309.4; 396/544
See application file for complete search history.

(56) References Cited

U.S. PATENT DOCUMENTS

| | | | | |
|---|---|---|---|---|
| 3,136,207 A * | 6/1964 | Gasser | ............... | G03B 19/18 396/360 |
| 4,458,354 A | 7/1984 | Munch | | |
| 5,708,874 A * | 1/1998 | Schrock | ............... | G03B 15/05 362/8 |
| 6,267,341 B1 * | 7/2001 | Fleming | ............... | B23Q 17/20 248/181.2 |
| 2005/0045784 A1 * | 3/2005 | Pitlor | ............... | H02G 3/20 248/206.5 |
| 2007/0183566 A1 | 8/2007 | Tsujita et al. | | |
| 2012/0305793 A1 | 12/2012 | Schiefer | | |
| 2014/0358275 A1 * | 12/2014 | Browne | ............... | F16M 13/022 700/214 |
| 2015/0083935 A1 | 3/2015 | Latham et al. | | |
| 2016/0015342 A1 | 1/2016 | Okuno | | |
| 2016/0045769 A1 * | 2/2016 | Amelia | ............... | A61N 5/1042 600/1 |
| 2016/0051210 A1 | 2/2016 | Kojima et al. | | |
| 2017/0106833 A1 * | 4/2017 | Marriott | ............... | B60R 22/48 |

(Continued)

FOREIGN PATENT DOCUMENTS

| | | |
|---|---|---|
| CN | 106725580 B | 2/2020 |
| CN | 110974268 A | 4/2020 |

(Continued)

OTHER PUBLICATIONS

PCT, International Search Report and Written Opinion of the International Searching Authority in PCT/US2021/051199, Jan. 20, 2022, 10 pages.

*Primary Examiner* — Christopher Garft
(74) *Attorney, Agent, or Firm* — Harness, Dickey & Pierce, P.L.C.

(57) ABSTRACT

An interface mount provides one or more attachment points each comprising an electromagnet operable to generate a magnetic field to hold an accessory including one or more magnetic members, allowing the accessory to be accepted by the interface mount.

19 Claims, 10 Drawing Sheets

(56) References Cited

U.S. PATENT DOCUMENTS

| | | |
|---|---|---|
| 2019/0090830 A1 | 3/2019 | Gao |
| 2020/0187885 A1 | 6/2020 | Tang et al. |
| 2021/0026409 A1* | 1/2021 | Miles .................... F16M 13/02 |
| 2021/0046885 A1* | 2/2021 | Jankura .................... F16B 2/04 |
| 2022/0108638 A1* | 4/2022 | Schuettke ............. G09F 9/3026 |

FOREIGN PATENT DOCUMENTS

| | | |
|---|---|---|
| GB | 715568 A | 9/1954 |
| WO | WO-2013080653 A1 | 6/2013 |
| WO | WO-2014192111 A1 | 12/2014 |

* cited by examiner

LATCHED

UNLATCHED

ELECTROMAGNETIC INTERFACE MOUNT FOR RADIATION MACHINES

TECHNICAL FIELD

This disclosure relates generally to radiation treatment and imaging. In particular, various embodiments of an interface mount with electromagnets to accept accessories for linear accelerators are described.

BACKGROUND

Interface mounts are used in radiation machines to accept accessories for e.g. modifying or characterizing beams or quality control during manufacturing, testing, or use of the radiation machines. Conventionally, an interface mount is externally attached to the treatment head of a radiation machine and includes frames or structures protruding from the treatment head toward the patient. Slots, pins and latches are used to receive, align, and secure an accessory to the interface mount. FIG. 1 depicts a conventional interface mount 12 attached to the treatment head 14 of a radiation machine 10. As illustrated, the conventional interface mount 12 includes structures sticking out of the treatment head 14, reducing the clearance between the treatment head 14 and the patient to be treated.

There are instances where increased clearance between the treatment head and the patient is desirable. A target to be irradiated may be located inside a large patient; increased clearance may be needed to position the target at the isocenter of the radiation machine. For advanced treatment such as volumetric modulated arc therapy (VMAT, RapidArc®), intensity-modulated radiation therapy (IMRT), stereotactic radiosurgery (SRS), and stereotactic body radiation therapy (SBRT) etc., gantry rotation during dose delivery may be required. Increased clearance helps ensure avoidance of collision, facilitate treatment planning, or enable advanced treatments.

Therefore, there are general needs for improved methods and apparatuses for mounting accessories. It would be desirable to have an interface mount that provides for increased patient clearance. It would be desirable to provide for an interface mount that allows for simple and safe attachment and removal of an accessory to and from a radiation machine.

SUMMARY

One embodiment of the disclosure provides for an apparatus including an interface mount for attachment to a radiation machine and an accessory. The interface mount provides at least one attachment point comprising an electromagnet operable to generate a magnetic field. The accessory comprises at least one member capable of being held by the magnetic field generated by the electromagnet, thereby allowing the accessory to be accepted by the radiation machine.

An example interface mount comprises three attachment "nests" or attachment points. Each attachment point may contain an electromagnet to provide holding force for a corresponding part on an accessory, which can be made from a ferromagnetic material in the shape of e.g. a "puck." In case of a power failure, each attachment point may have a safety latch that mechanically engages and holds the accessory in place. The latch can be spring-loaded and may be moved to an unlatched position by a solenoid. The latch may have a small ramp to allow attachment of the accessory without the need for powering the solenoid to move the latch to the unlatched position. The latch position can be monitored by a proximity sensor indicating the latched and unlatched state. Each attachment point may also contain a second proximity sensor to detect the presence or proper seating of the accessory. The electromagnet can be suspended on a spherical bearing to provide for good planar alignment with the accessory. A bolt holding the electromagnet to a housing can be hollow and the head of the bolt may have features for precise accessory alignment such as X-Y positioning, clocking, and/or Z leveling. A multicolor LED may be disposed inside the bolt to emit light toward the accessory where the light hits a diffuser visible to the user as an indicator of status of the machine and/or the accessory. A connector can be provided near one or more attachment points to connect with the attached accessory for passing communication signals and ID codes. The ID code of an accessory can be passed to the system via an ID reader module containing sensors. The ID code of an accessory can be in a separate module attached to the accessory and may comprise e.g. permanent magnets arranged in a particular pattern.

This Summary is provided to introduce selected embodiments in a simplified form and is not intended to identify key features or essential characteristics of the claimed subject matter, nor is it intended to be used as an aid in determining the scope of the claimed subject matter. The selected embodiments are presented merely to provide the reader with a brief summary of certain forms the invention might take and are not intended to limit the scope of the invention. Other aspects and embodiments of the disclosure are described in the section of Detailed Description.

BRIEF DESCRIPTION OF THE DRAWINGS

These and various other features and advantages of the disclosure will become better understood upon reading of the following detailed description and the appended claims in conjunction with the accompanying drawings, where:

DETAILED DESCRIPTION OF EMBODIMENTS

Figure 1:
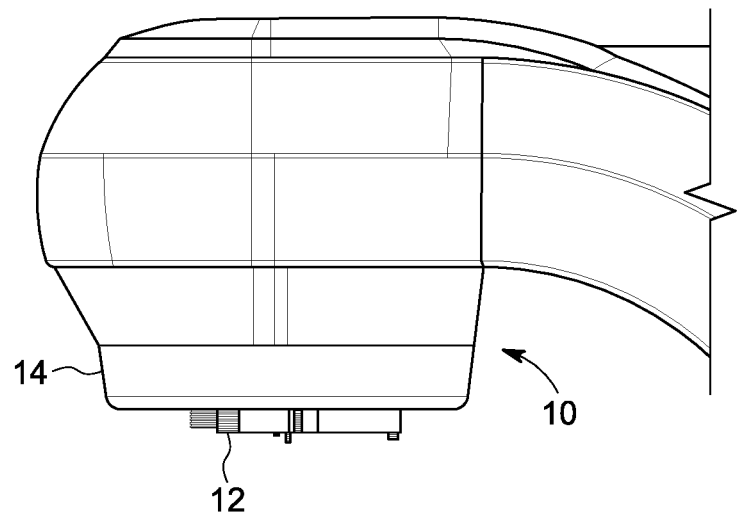
FIG. 1 is a side partial view of a radiation machine comprising a conventional interface mount.

With reference to FIGS. 2-15, where like reference numerals denote like parts, various embodiments of an interface mount and a radiation machine including the interface mount are described. In general, an example interface mount comprises one or more electromagnets to hold an accessory. The use of electromagnets eliminates the need for frames or supporting structures protruding toward the isocenter of a radiation machine. As such, the maximal clearance between the patient and the radiation machine can be achieved. The attachment of an accessory to the interface mount is simple and automatic by bringing the accessory close to one or more attachment points in the interface mount. The removal of the accessory can be initiated by pushing one or more switches, which can be integrated in the accessory. In case of a power failure, safety latches can mechanically hold the accessory in place. The alignment of the accessory can be facilitated by the use of spherical bearings and electromagnet holding bolts, monitored by sensors, and indicated by multicolor LEDs.

Figure 2A:
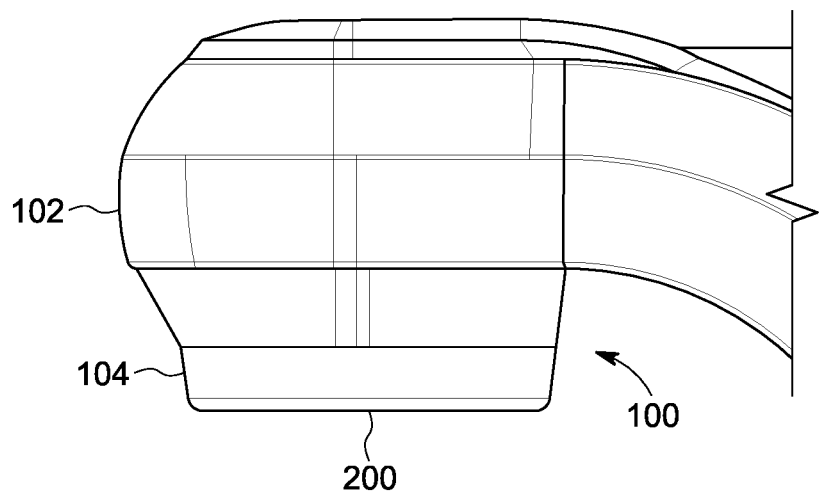
FIG. 2A is a side partial view of a radiation machine comprising an interface mount according to embodiments of the disclosure.
Figure 2B:
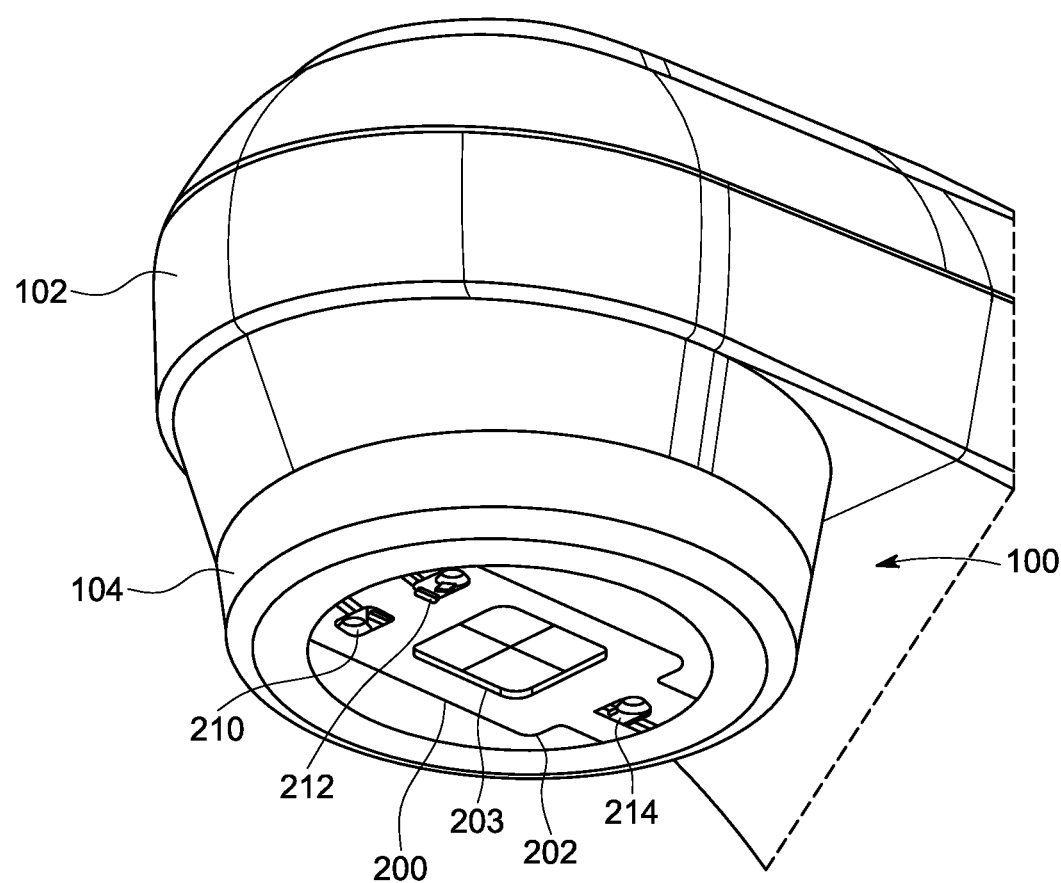
FIG. 2B is a bottom isometric partial view of the radiation machine of FIG. 2A, emphasizing the example interface mount of the disclosure.

FIGS. 2A-2B depict an example radiation machine 100 in which various embodiments of the disclosure can be implemented. It should be noted that while embodiments of an interface mount are described in connection with a radiotherapy machine, the interface mount of the disclosure can also be implemented in a diagnostic system, a simulation system, a research and developmental system, or any other suitable radiation system. Embodiments of the disclosure are particularly useful in a system adapted to perform intensity-modulated radiation therapy (IMRT) or volumetric modulated arc therapy (VMAT), stereotactic radiotherapy (SRS) or stereotactic body radiation therapy (SBRT). Embodiments of the disclosure can also be practiced in any systems including two devices or subassemblies which need to mate for a short or long period of time.

With reference to FIGS. 2A-2B, the radiation machine 100 includes a gantry 102 enclosing a radiation source (not shown). The radiation source may be a source producing or emitting photons, or protons, or heavy ions, or electrons, or other types of radiation. By way of example, the radiation machine 100 may comprise a linear accelerator including a metallic target configured to produce x-rays upon impingement by electrons. The radiation machine 100 may also include various devices or components for shaping, modifying, and monitoring the properties of the radiation produced by the radiation source. For example, various collimation devices such as collimation blocks and multileaf collimators may be disposed in a treatment head 104, to define or modify the shape, size, and/or intensity of the radiation produced by the radiation source. The gantry 102 can be a C-arm gantry, a ring gantry, or a robotic arm gantry, and rotatable about one or more rotation axes. The operation of the radiation machine 100, including the rotation of the gantry and operations of various devices inside the gantry and treatment head can be controlled by a control system (not shown).

Figure 4:
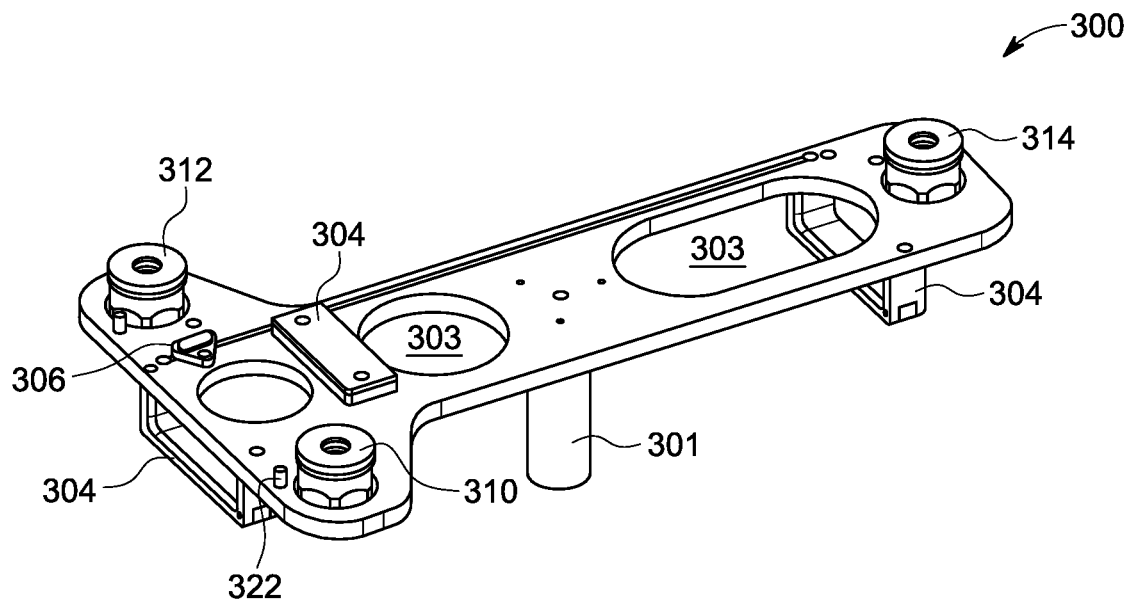
FIG. 4 is a top isometric view of an example accessory according to embodiments of the disclosure.

With reference to FIGS. 2A-2B, the radiation machine 100 includes an interface mount 200. The interface mount 200 serves to accept an accessory to the treatment head 104 of the radiation machine 100 for various applications. As used herein, the term "accessory" refers to an assembly or subassembly including a component e.g. for shaping or modifying a beam, or a device or tool for characterizing a beam, detecting alignment of a beam, or for quality control during the use, testing, or manufacturing of a radiation machine. Example components for shaping or modifying a beam include but are not limited to collimators such as SRS cones, electron applicators, beam filters, or the like. Example devices or tools for quality control include but are not limited to ion chamber (IC) profilers, front pointers, and so on. According to embodiments of the disclosure, an accessory may include one or more members capable of being held by one or more electromagnets in the interface mount, e.g. one or more members constructed from a magnetic material as will be described in greater detailed below. FIG. 4 depicts an example accessory 300 carrying a beam shaping component 301 e.g. an SRS cone according to embodiments of the disclosure.

With reference to FIGS. 2A-2B, the interface mount 200 may include a plate or frame 202 having an opening 203 for passing a radiation beam and attachment points 210, 212, 214 for holding an accessory. Three attachment points are shown in FIG. 2B for illustration purpose. One of ordinary skill in the art will appreciate that fewer or more than three attachment points may be used to perform the functions of the interface mount described in the disclosure. In some instances, only one attachment point in an interface mount is sufficient. The plate 202 of the interface mount 200 may be attached to the radiation machine 100 as an integral part of the treatment head 104. For example, the plate 202 of the interface mount 200 may further serve as a supporting frame for an multileaf collimator inside the treatment head 104. Alternatively, the interface mount 200 including a plate 202 and parts on the plate can be attached to the treatment head using other suitable means such as bolts, fasteners, or the like. Once the interface mount 200 is installed, no components or structures protruding from the treatment head 104 would be needed for accepting an accessory, as better viewed in FIG. 2A. As such, the maximal or increased clearance between the treatment head 104 of the radiation machine 100 and the patient can be achieved by the interface mount 200 of the disclosure.

Figure 3:
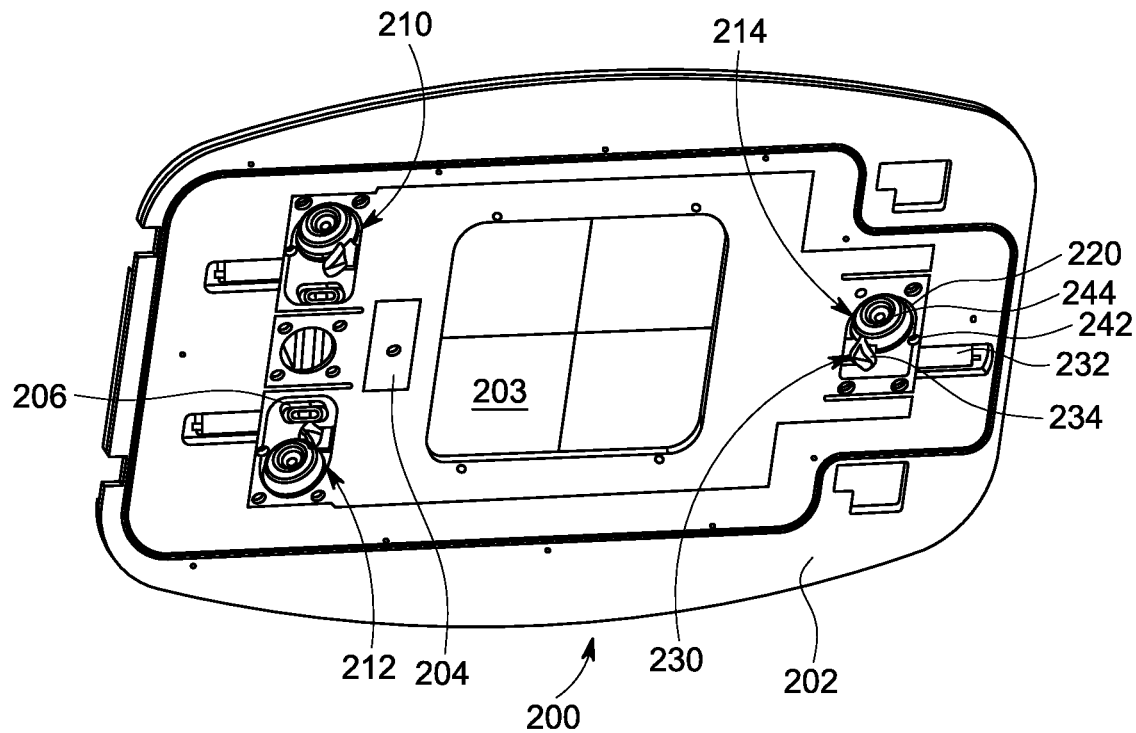
FIG. 3 is a bottom view of an example interface mount according to embodiments of the disclosure.

FIG. 3 is a bottom view of an example interface mount 200 of the disclosure. FIG. 4 is a top isometric view of an example accessory 300 of the disclosure which can be accepted by the interface mount 200 of FIG. 3. As shown, the example interface mount 200 includes multiple attachment nests or attachment points 210, 212, 214. Correspondingly, the example accessory 300 includes multiple members 310, 312, 314 to be received in or held by the attachment points 210-214 in the interface mount 200. According to embodiments of the disclosure, an attachment point e.g. 214 in the interface mount 200 includes an electromagnet 220 operable to generate a magnetic field. The example accessory 300 includes a member e.g. 314 capable of being held by the magnetic field generated by the electromagnet 220. A safety lock 230 may be provided at the attachment point 214 to mechanically hold the accessory 300 in case of a power failure. The safety lock 230 may include a solenoid 232 operating a safety latch 234. At the attachment point 214, a first sensor e.g. a proximity sensor 240 may be provided to monitor the state of the safety latch 234, and a second sensor e.g. a proximity sensor 242 may be provided to monitor the presence or alignment of the accessory 300 (see also FIGS. 6, 11A-11B, and 13 for sensor 240). A multicolor LED 244 may be provided in the attachment point 214 to indicate the state of the accessory alignment or of the machine. The electromagnet 220, safety lock 230, proximity sensors 240, 242, and other parts at an attachment point 210-214 will be described in greater detail below in conjunction with other figures. In FIGS. 3-4, three attachment points 210-214 in the interface mount 200 and three magnetic members 310-314 on an accessory 300 are shown. According to embodiments of the disclosure, at each of the attachment points 310-314, an electromagnet 220, a safety lock 230, a first proximity sensor 240, and a second proximity sensor 242 may be provided. In FIGS. 3 and 4, reference numeral 204 denotes an ID reader module optionally provided on the interface mount 200 to detect an ID code module 304 optionally provided on the accessory 300, to be described further below. Reference numeral 206 denote a connector on the interface mount 200 for connecting with a connector 306 on the attached accessory 300 to pass communication signals and ID codes.

Figure 5:
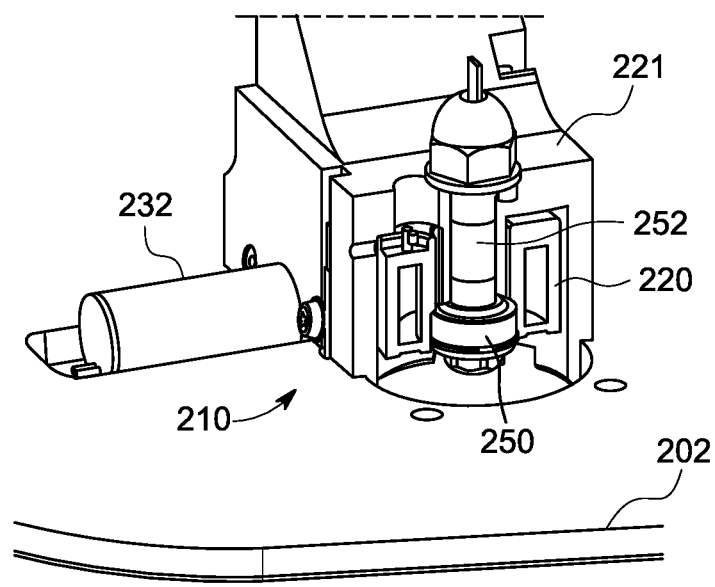
FIG. 5 is a top cutaway partial view of an example interface mount of the disclosure, emphasizing some parts at an attachment point.
Figure 6:
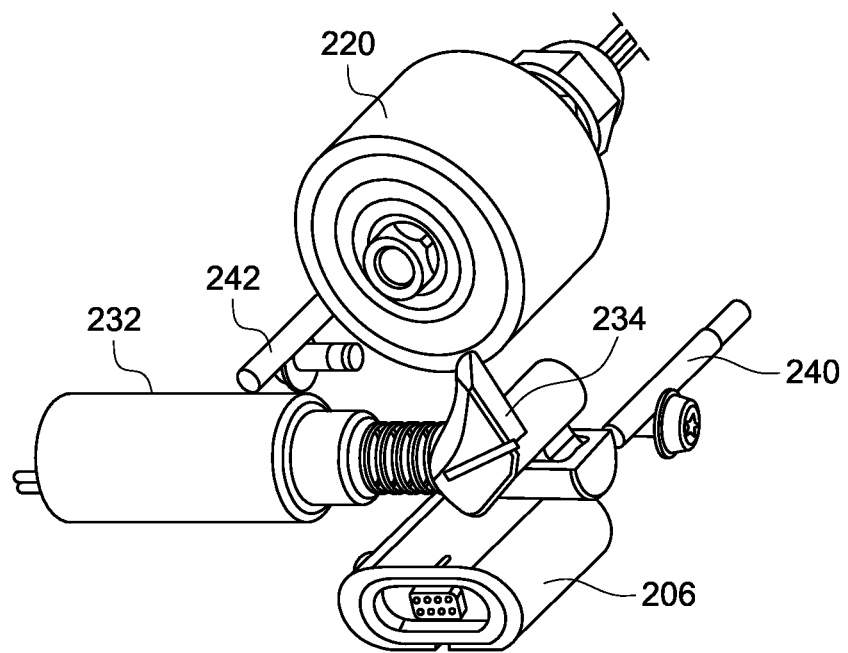
FIG. 6 is a cutaway view showing some parts and the spatial relationship of the parts at an attachment point.
Figure 7:
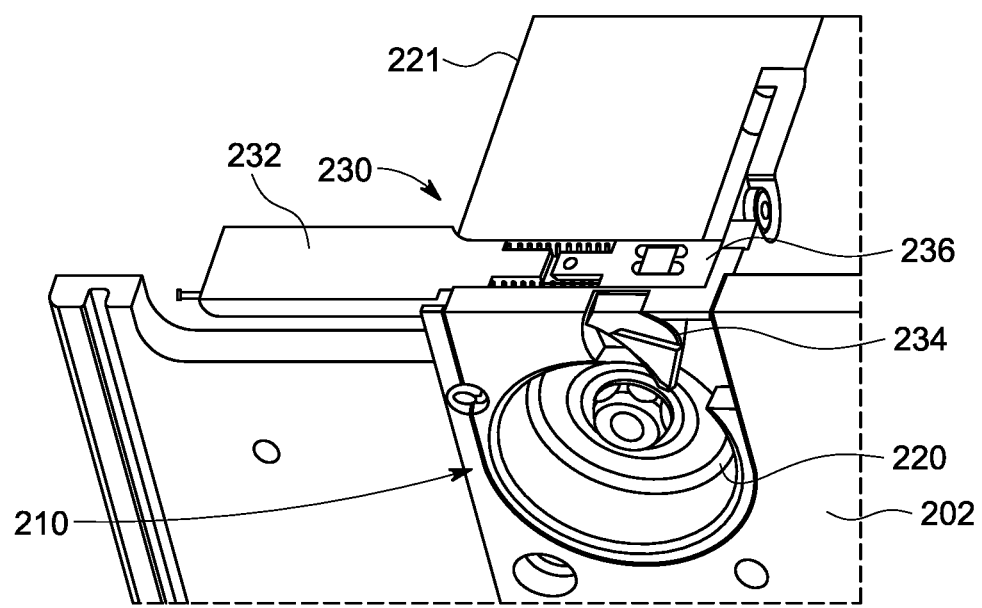
FIG. 7 is a bottom cutaway partial view of an example interface mount of the disclosure, emphasizing an attachment point and a safety lock.
Figure 8:
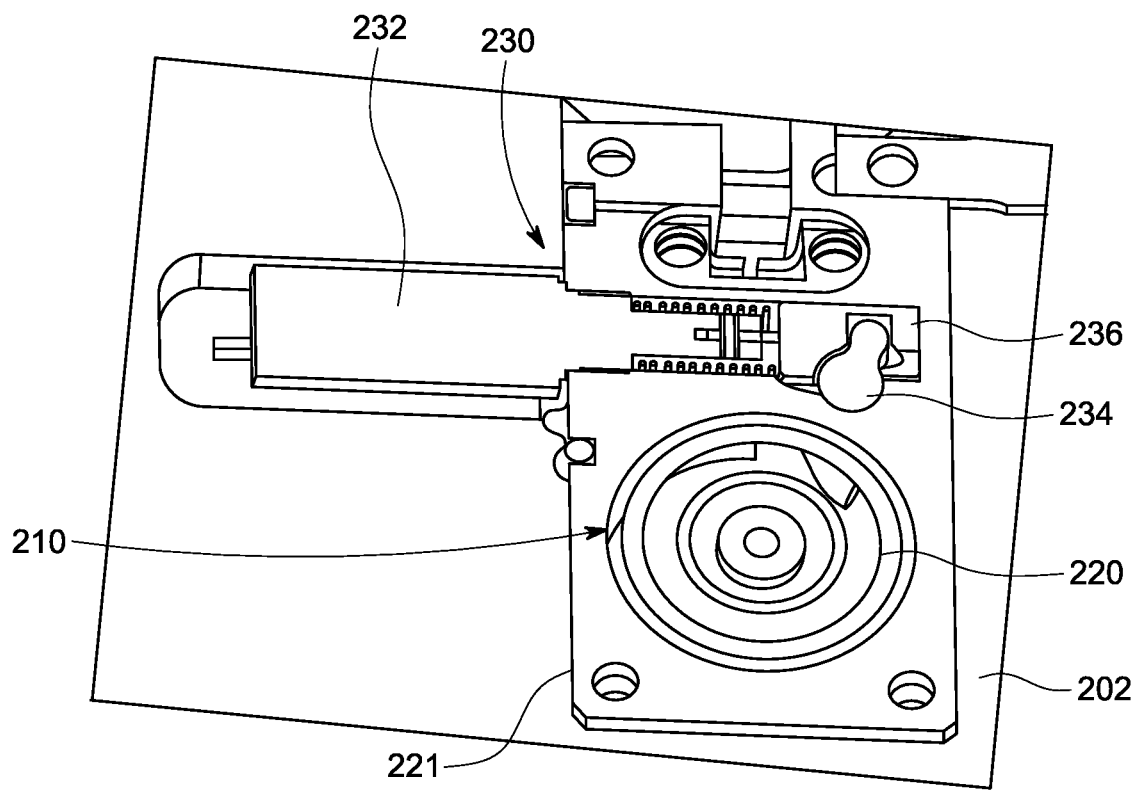
FIG. 8 is a bottom cross-sectional partial view of an example interface mount of the disclosure, emphasizing an attachment point and a safety lock.

FIG. 5 is a top cutaway partial view of an example interface mount 200 of the disclosure, emphasizing some parts at an attachment point 210. As shown, an electromagnet 220 can be supported in a housing 221 mounted on the interface plate 202. A spherical bearing 250 and a bolt or elongate member 252 can be used to support and secure the electromagnet 220 to the housing 221, to be described in greater detail below. FIG. 6 is a cutaway view showing with greater clarity an electromagnet 220 and the spatial relationship between the electromagnet 220 and some other parts at the attachment point 210, including a solenoid 232, a safety latch 234, a first sensor 240 e.g. a proximity sensor for monitoring the state of the safety latch 234, a second sensor 242 e.g. a proximity sensor for monitoring an accessory 300, and an electrical connector 206. FIG. 7 is a bottom cutaway view showing the attachment point 210 and a safety lock 230 with greater clarity. As shown, an electromagnet 220 is recessed in the housing 221, which includes a bottom plate generally flush with the interface plate 202. The parts of the safety lock 230, including a solenoid 232, a safety latch 234, and a drive member 236 coupling the solenoid 232 and the safety latch 234 are supported or housed in the housing 221 above the interface plate 202. Once installed, no parts protrude from the housing 221, allowing to achieve the maximal clearance between the treatment head and the patient. FIG. 8 is a bottom cross-sectional view showing the attachment point 210 and the spatial relationship among an electromagnet 220, a safety lock 230 including a solenoid 232, a safety latch 234, a drive member 236, and other parts in a housing 221 mounted on an interface plate 202. The operation of the electromagnet 220 and safety lock 230 will be described in greater detail below in conjunction with other figures.

Figure 9:
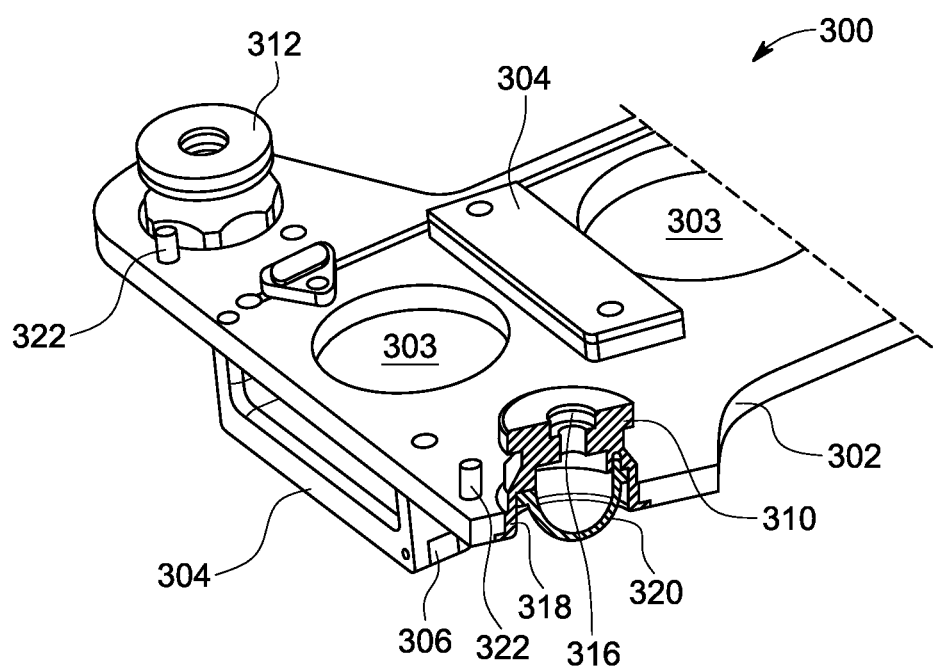
FIG. 9 is a top isometric partial view of an example accessory according to embodiments of the disclosure.
Figure 10:
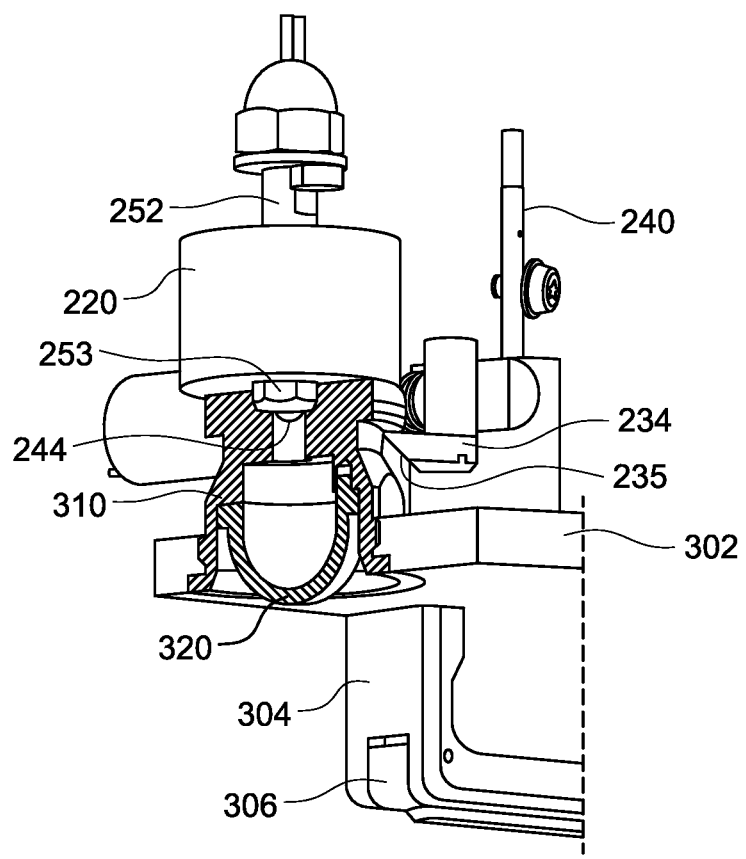
FIG. 10 is a cutaway view showing an energized electromagnet at an attachment point holding a magnetic member on an example accessory according to embodiments of the disclosure.

With reference now to FIGS. 9-10, according to embodiments of the disclosure, at least one attachment point 210 in the interface mount 200 includes an electromagnet 220 operable to generate a magnetic field. The accessory 300 includes at least one member 310 capable of being held by the magnetic field generated by the electromagnet 220, allowing the accessory 300 to be attracted or accepted by the interface mount 200. Electromagnets are known in the art. Briefly and generally, an electromagnet generates a magnetic field by an electrical current. An electromagnet may include a coil of wires wound on an iron, steel or other metal core. A magnetic field is generated when electrical current flows through the wires, creating a holding force to attract a member made of a magnetic material. The magnetic field is removed when the electrical current is turned off, allowing the member of a magnetic material to be released from the electromagnet.

With reference still to FIGS. 9-10, an example member 310 on the accessory 300 can be made from a magnetic material. In this disclosure, the term "magnetic member" may be used to refer to a member made of a magnetic material. Suitable magnetic materials include but are not limited to a ferromagnetic material, a ferrimagnetic material, a paramagnetic material, a diamagnetic material, and an antiferromagnetic material. Suitable ferromagnetic materials include but are not limited to a material comprising iron, nickel, cobalt, and their alloys. The magnetic member 310 can be constructed in various sizes and shapes. By way of example, the magnetic member 310 may include an annular portion in the shape of e.g. a "puck" for engaging with an electromagnet 220 and a bottom portion configured to secure the magnetic member 310 to a plate 302 by a suitable means such as flanges, fasteners, bolts, or the like. The magnetic member 310 may include a groove under the annular portion to allow a safety latch 234 to mechanically engage and hold the magnetic member 310, and thus lock the accessory 300 in case of a power failure. The peripheral side surface between the top surface of the annular portion and the groove of the magnetic member 310 may be rounded or curved to facilitate pushing against a ramp 235 on the safety latch 234 in bringing the magnetic member 310 close to the electromagnet 220, to be described further below. The magnetic member 310 may be provided with a counterbore 316 in the annular portion configured to receive an end portion 253 of an elongate member 252 supporting the electromagnet 220. The magnetic member 310 may also include a recess 318 in the bottom portion to house a light diffuser 320 for diffusing light emitted from a multicolor LED 244 disposed in the elongate member 252, to be described in greater detail below.

With reference still to FIGS. 9-10, a pin member 322 may be provided adjacent to a magnetic member 310. The pin member 322 can be detected by a proximity sensor 242 (FIGS. 3 and 6) at an attachment point 210 in the interface mount 200 so that the presence and alignment of the accessory 300 can be detected. Preferably, adjacent to each of the magnetic members 310-314 is provided with a pin member 322 to ensure precise detection of the accessory alignment. The accessory 300 may include an ID code module or identifier 304 to provide identification information of the accessory. The ID code can be detected by an ID reader 204 on the interface mount 200, which can then transmit the ID code to a control system, to be described further below. The accessory 300 may also include one or two handles 304 to aid the user in bringing the accessory 300 close to the interface mount 200 and removing the accessory 300 from the interface mount 200. One or two switches 306 such as momentary switches can be integrated in the handles 304 to control the power to the solenoids 232 of safety locks 230, allowing the accessory 300 to be released from the electromagnets 220, to be described in greater detail below.

Alternatively, the switch(es) 304 can be disposed at other locations on the accessory or interface mount. The accessory plate 302 may have cutouts 303 to reduce the weight of the accessory 300.

Figure 11A:
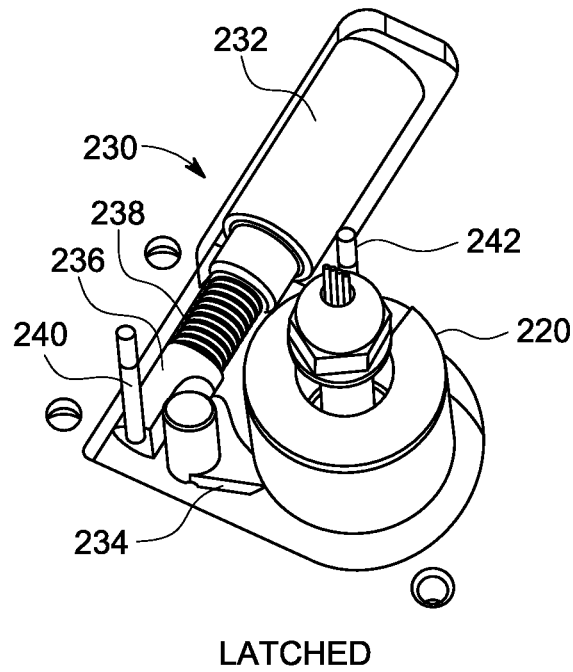
FIGS. 11A-11B are top cutaway partial views of an example interface mount of the disclosure, emphasizing a safety lock at an attachment point.
Figure 11B:
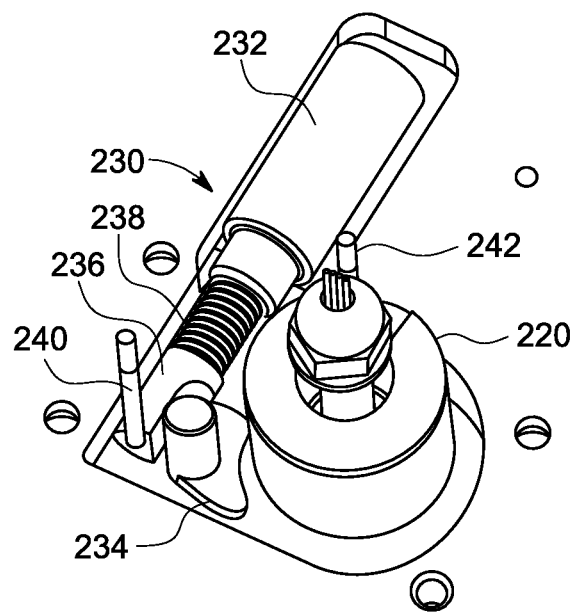
Figure 12A:
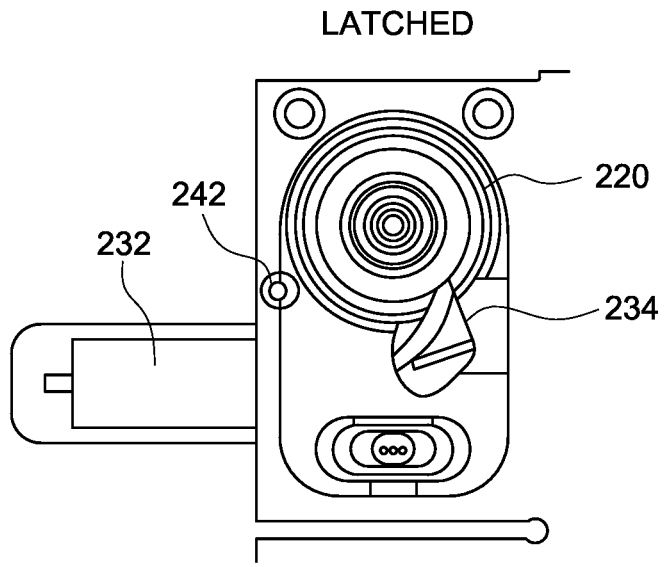
FIGS. 12A-12B are bottom partial views of an example interface mount of the disclosure, emphasizing a safety lock at an attachment point.
Figure 12B:
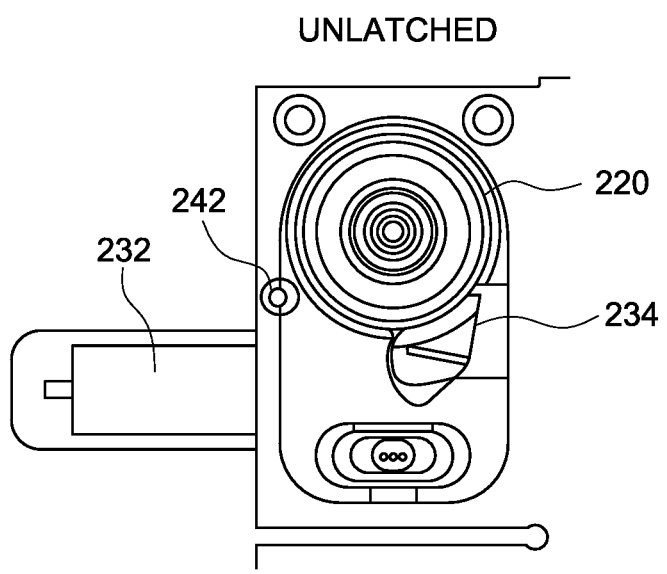

With reference now to FIGS. 11A-11B and 12A-12B, the interface mount 200 may include at least one safety lock 230 at an attachment point operable to lock the accessory 300 accepted by the interface mount 200. Preferably, at each of the attachment points 210-214 is provided with a safety lock 230. According to embodiments of the disclosure, the at least one safety lock 230 comprises a spring-loaded latch member 234 movable between a latched position and an unlatched position relative to a magnetic member on the accessory. As shown in FIGS. 11A-11B, an example safety lock 230 includes a latch member 234, a drive member 236 coupled to the latch member 234, a spring 238 coupled to the drive member 236, and a solenoid 232 operable to compress and release the spring 238. The solenoid 232 is operable to move the drive member 236 by compressing and releasing the spring 238. The motion or travel of the drive member 236 in turn moves e.g. translates or rotates the latch member 234, allowing the latch member 234 to be positioned at a latched position and an unlatched position. See also FIGS. 7-8. Solenoids are known in the art. Briefly and generally, a solenoid is an electromagnetic device that converts electrical energy into a mechanical force or motion. A solenoid generally includes an electrical coil wound in a helical pattern and a plunger or a ferromagnetic actuator sliding "IN" or "OUT" of the coils body. When the coil is connected to electric current, a magnetic field is created causing the plunger to slide "IN" or "OUT" of the coils body, depending on configuration of the solenoid. When electricity to the solenoid is turned off, the magnetic field is removed allowing the plunger to slide "OUT" or "IN" the coils body. FIG. 11A shows a locked state of the safety lock 230 or latched position of the latch member 234. FIG. 11B shows an unlocked state of the safety lock 230 or unlatched position of the latch member 234. FIGS. 12A-12B are bottom views showing the locked state and unlocked state respectively. In alternative embodiments, the safety lock 230 may include a servo motor operable to move e.g. translate or rotate the latch member 234, between a latched position and an unlatched position.

According to embodiments of the disclosure, the safety lock 230 can be configured such that when the solenoid 232 is unpowered, the safety lock 230 is in a locked state or the latch member 234 is in a latched position, whereas when the solenoid 232 is powered, the safety lock 230 is in an unlocked state or the latch member 234 is in an unlatched position. In such configuration, when a power failure occurs, the safety lock 230 remains in the locked state to mechanically hold the accessory 300, preventing the accessory 300 from falling from unenergized electromagnets 220. In a normal operation, to remove an installed accessory 300 from the electromagnets 220, the solenoids 232 can be powered, allowing the safety locks 230 to open to remove the accessory 300 released by the electromagnets 220. In an initial stage of operation, the safety lock 230 may be set in the locked state but the user can bring an accessory 300 close to the interface mount 200 by pushing against the ramp 235 on the safety latch 234, as better viewed in FIG. 10, without the need to power the solenoids 232 to open the safety lock 230. According to embodiments of the disclosure, a sensor 240 e.g. a proximity sensor may be provided in the interface mount 200 to detect the state of the safety lock 230 e.g. by sensing the position of the latch member 234, and transmit a signal to a control system indicating the state of the safety lock.

Figure 13:
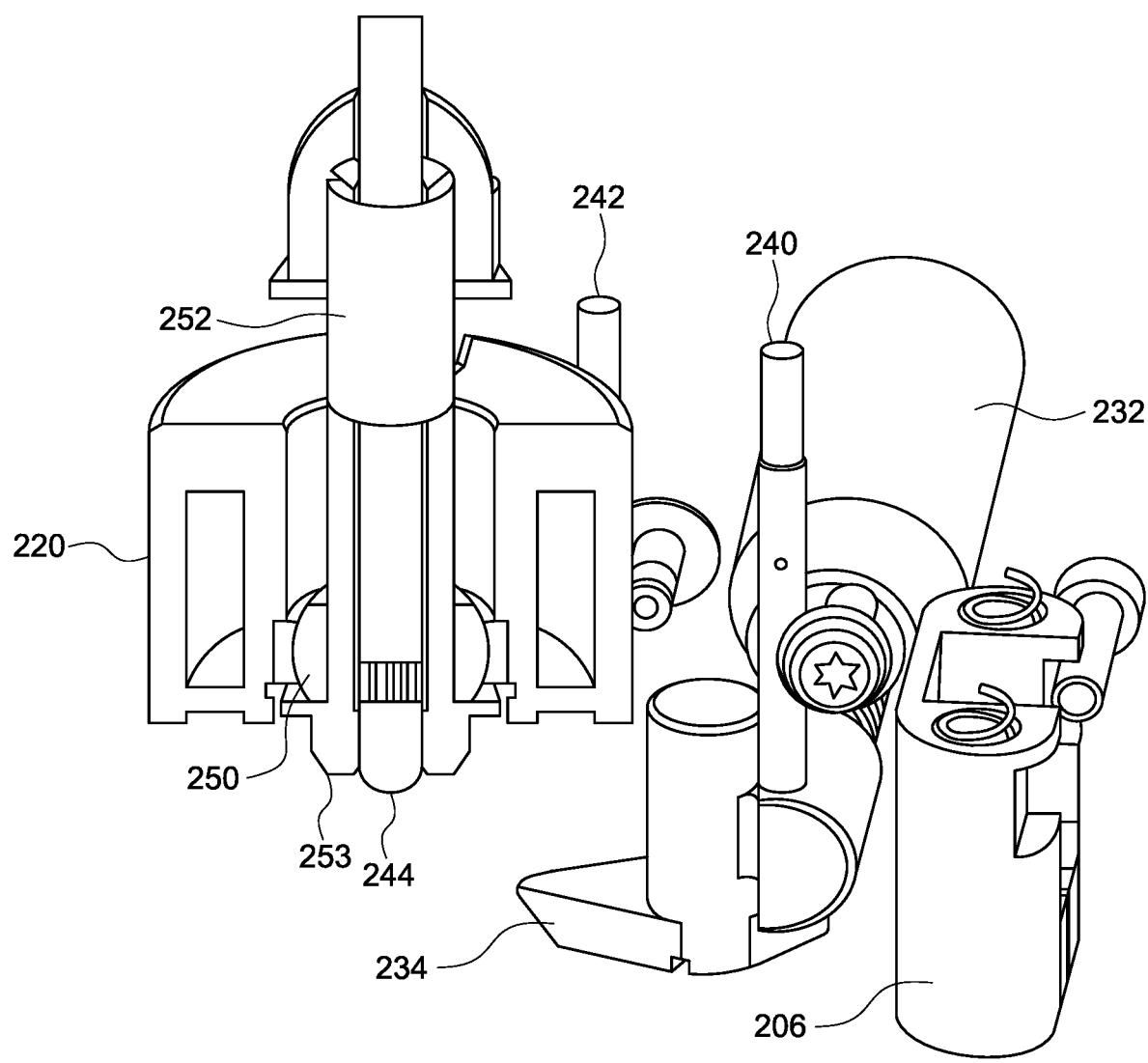
FIG. 13 is a cutaway view, emphasizing a spherical bearing in an electromagnet and a bolt securing the electromagnet to a housing.
Figure 14:
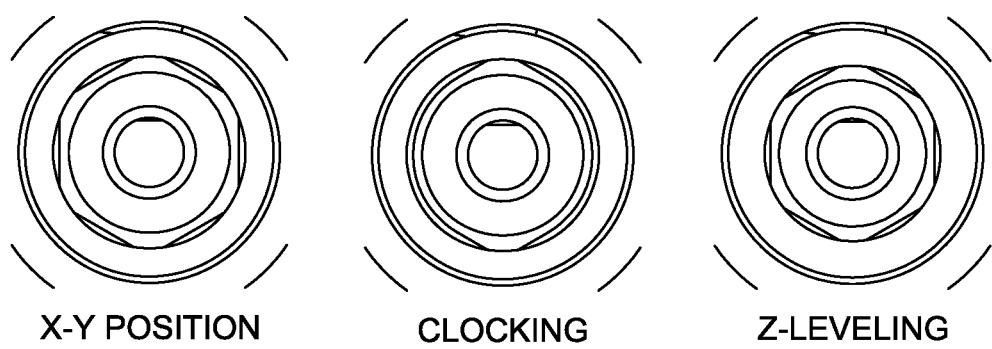
FIG. 14 shows example head features of example bolts used for positioning an accessory.
Figure 15:
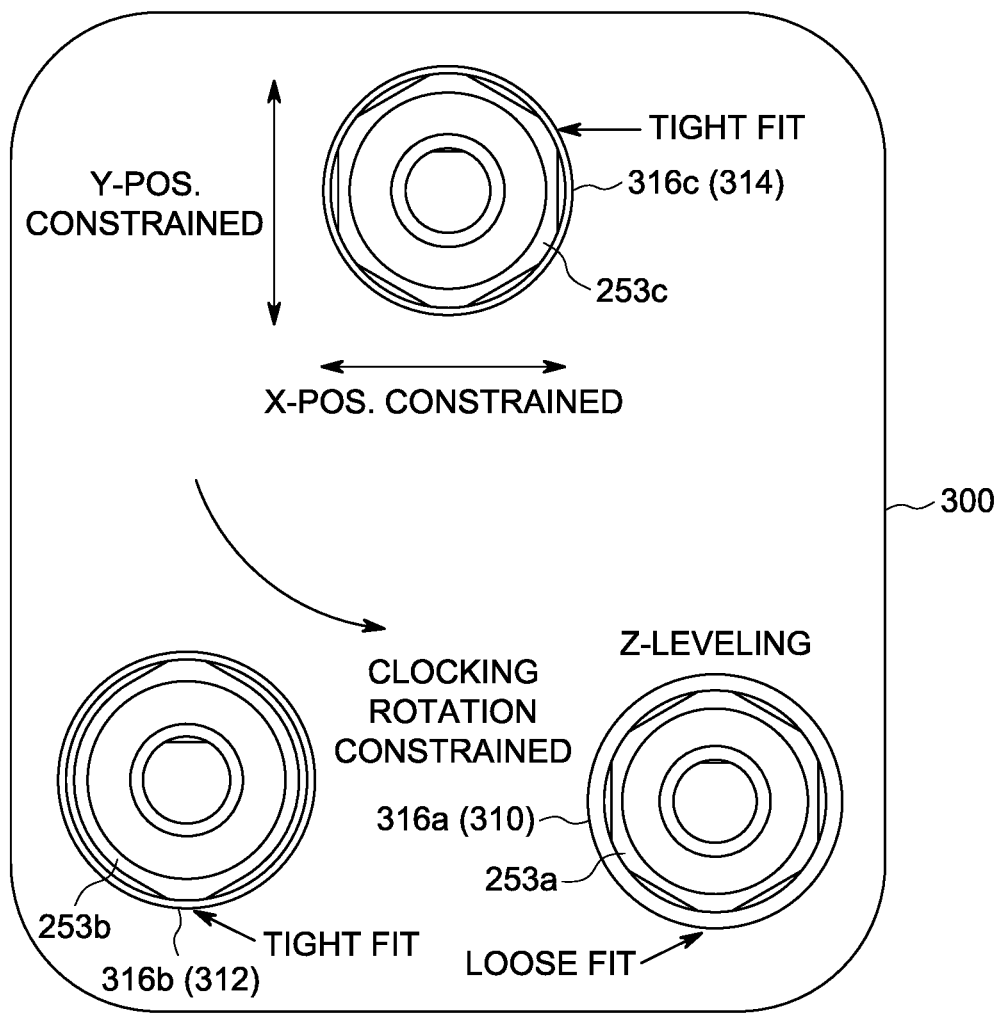
FIG. 15 is a cross-sectional view showing example bolt heads received in counterbores of example magnetic members on an example accessory.

With reference to FIGS. 13-14, according to embodiments of the disclosure, an electromagnet 220 can be supported by a bolt or elongate member 252 and a spherical bearing 250. The spherical bearing 250 can be disposed in a channel in the electromagnet 220 and received on the elongate member 252, allowing the electromagnet 220 to be suspended and tilt in receiving the accessory 300 and thus providing for good planar alignment with the accessory 300. The elongate member 252 may couple the electromagnet 220 e.g. at the bottom of the electromagnet 220 and be secured to a housing 221 by any suitable means such as threading, nuts, fasteners, or the like (see also FIG. 5). The elongate member 252 includes an end portion 253 configured to be received in a counterbore 316 in a magnetic member 310-314 of the accessory 300, as better viewed in FIGS. 9-10. The end portion 253 of an elongate member 252 and the counterbore 316 of a magnetic member 310-314 may be provided with features to aid in positioning, leveling, or clocking of the accessory 300 during accessory installation. FIG. 14 shows example features that the end portion 253 of an elongate member 252 may be provided. In certain embodiments, an interface mount 200 may include multiple e.g. three attachment points 210-214 each including an electromagnet 220. The multiple e.g. three electromagnets 220 may be supported by multiple e.g. three elongate members 252 and three spherical bearings 250 respectively. The end portions 253 of the three elongate members 252 may have different features, e.g., one end portion having a feature for X-Y positioning, one end portion having a feature for clocking, and one end portion having a feature for Z-leveling as shown in FIG. 14. The counterbores 316 in the multiple e.g. three magnetic members 310-314 on the accessory 300 may be provided with corresponding features. Collectively, the features on the end portions 253 of the three elongate members 252 and in the counterbores 316 of the three magnetic members 310-314 provide precise positioning, leveling, and clocking. FIG. 15 is a cross-sectional view showing example bolt heads 253a, 253b, 253c received in counterbores 316a, 316b, 316c of magnetic members 310, 312, 314 on accessory 300. As shown, bolt head 253a and counterbore 316a in magnetic member 310 may be configured to provide proper Z-leveling. Bolt head 253b and counterbore 316b in magnetic member 312 may be configured to provide proper clocking. As an example, bolt head 253b may be provided with diamond pin-like features and counterbore 316b in magnetic member 312 may be provided with corresponding slot features such that when bolt head 253b is properly aligned with and tightly fits in counterbore 316b in magnetic member 312, rotation of accessory 300, clockwise or counterclockwise, is constrained. Bolt head 253c and counterbore 316c in magnetic member 314 may be configured to provide proper X-Y positioning. For example, bolt head 253c may be provided with a plurality of pin-like features and counterbore 316c in magnetic member 314 may be provided with corresponding slot features such that when bolt head 253c is properly aligned with and tightly fits in counterbore 316c in magnetic member 314, motions of accessory 300 in X-Y directions are constrained. A sensor 242 e.g. a proximity sensor may be provided at an attachment point, or preferably at each of the multiple attachment points 210-214, to monitor accessory alignment. A pin member 322 may be provided adjacent to a magnetic member on the accessory, or preferably next to each of the multiple magnetic members 310-314 on the accessory 300, to be detected by a sensor or sensors 242 in the interface mount 200 for precise detection of accessory alignment.

With reference still to FIGS. 13-14, the elongate member 252 or at least a section of the elongate member 252 may be hollow or provided with a channel. A light source e.g. a multicolor LED 244 may be disposed in the channel of the elongate member 252 to emit light indicating the status of accessory alignment. By way of example, green light may be used to indicate correct accessory alignment, red light to indicate misalignment, and so on. A light diffuser 320 disposed in a magnetic member 310-314 (see FIG. 10) can diffuse the light emitted by the multicolor LED 244, allowing the user to observe the indicator light more easily.

Returning to FIGS. 3-4, according to embodiments of the disclosure, the interface mount 200 may include a detector 204 to detect an identifier 304 provided on an accessory 300. The identifier 304 provides identification information of an accessory e.g. a particular beam shaping or modifying component 301 carried by the accessory, a particular device or tool 301 carried by the accessory for beam characterization or quality control, etc. The identifier 304 on the accessory 300 and the detector 204 on the interface mount 200 allow the control system of the radiation machine 100 to verify if a correct accessory as planned is attached to the interface mount 200. Upon verification that a correct accessory is attached, the control can adapt its operation based on the actually attached accessory. If it is verified that an incorrect accessory is attached, a warning signal may be generated by the control and the system interlocked. The identifier 304 may be an ID code module encoded with identification information of the accessory 300, and the detector 204 may be an ID reader capable of reading the ID code. By way of example, the identifier 304 may include magnetic elements arranged in a particular pattern (code). The detector 204 may include an array of sensors capable of detecting electromagnetic fields generated by the magnetic elements. As another example, the identifier 304 may include a passive or active transmitter providing an output signal that can be detected by a receiver or sensor 204 such as an ultrasound sensor, capacitive sensor, or a camera e.g. infrared camera. As another example, the identifier 304 may include a radio frequency identification (RFID) tag which can be detected by an RFID reader 204. As a further example, the identifier 304 may include a fiducial marker which can be detected by an imaging system 204. The identifier 304 may act or function as a binary data record and the detector 204 may act or function as a binary data reader.

Various embodiments of an interface mount to accept accessories for a linear accelerator have been described in conjunction with FIGS. 2-15. Advantageously, the use of electromagnets maximizes the clearance between the treatment head and the patient and simplifies the attachment and removal of the accessories. Safety locks ensure that an accessory remain locked in case of a power failure. Spherical bearings aid in accessory alignment, which can be monitored by sensors and indicated by multicolor LEDs.

With reference to FIGS. 3-4, example operation or use of an example interface mount 200 and the accessory 300 of the disclosure is now described. At the start, the safety locks 230 at the attachment points 210-214 in the interface mount 200 may be set such the latches 234 are initially in latched positions. The ramps on the safety latches 234 allow the user to push an accessory 300 against the spring-loaded latches 234 and to seat the accessory 300 at the attachment points 210-214 without the need to energize the solenoids 232. The action of latch changes can be detected by the latch proximity sensors or first sensors 240, sending signals to the control system. Depending on a combination of signals from the latch sensors 240, the control system may send signals to energize the electromagnets 220 in the attachment points 210-214. In certain embodiments, a combination of signals from at least two proximity sensors 240 is used to energize the electromagnets 220 in order to avoid a situation where a safety latch is accidentally pushed by the user or a tool. In some embodiments, a combination of signals from three or all of the latch sensors 240 is used to energize the electromagnets 220.

The installation sensors or second sensors 242 provide signals of successful or failed installation depending on whether a precise accessory alignment is achieved. The control sends signals to the multicolor LEDs 244 to indicate the state of installment. The LEDs 244 may emit green light indicating a successful accessory installation and then turn off several seconds thereafter. In case of a failed accessory installation, the LEDs 244 may emit red light, which should remain on as long as the accessory 300 is attached or held to the interface mount 200. The red indicator light of LEDs 244 can be turned on if the state of any of installation sensors 242 and latch sensors 240 changes, in which case, the operation of the radiation machine 100 should be aborted.

To remove the accessory 300 after a successful installation or use, the user may simultaneously press the momentary switches 306, which can be integrated in the handles 304 of the accessory 300. This will energize the solenoids 232, moving the safety latches 234 to unlatched positions. The latch proximity sensors or first sensors 240 may detect the change of latch positions and the control send signals to turn off the electromagnets 220. A small pulse of opposite current may be applied to the electromagnets 220 to eliminate any remnant magnetism that may continue to hold the accessory 300 attached to the interface mount 200. Then, the accessory 300 can be removed. The installation proximity sensors or second sensors 242 may detect the absence of the accessory 300, and the control send signals to turn off the power to the solenoids 232, allowing the safety latches 234 to return to the latched positions by the spring actions.

Various embodiments of an apparatus comprising an interface mount and an accessory have been described with reference to the figures. It should be noted that some figures are not necessarily drawn to scale. The figures are only intended to facilitate the description of specific embodiments and are not intended as an exhaustive description or as a limitation on the scope of the disclosure. Further, in the figures and description, specific details may be set forth in order to provide a thorough understanding of the disclosure. It will be apparent to one of ordinary skill in the art that some of these specific details may not be employed to practice embodiments of the disclosure. In other instances, well known components may not be shown or described in detail in order to avoid unnecessarily obscuring embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. The term "first" or "second" is used to distinguish one element from another in describing various similar elements and should not be construed as in any particular order unless the context clearly dictates otherwise. Relative terms such as "upper," "above," "top," "over," "on," "below," "under,"

"bottom," "lower" or similar terms may be used herein for convenience in describing relative positions or spatial relationships in conjunction with various embodiments. The use of the relative terms should not be construed as to imply a necessary positioning or orientation of the structures or portions thereof in manufacturing or use, and to limit the scope of the invention.

Those skilled in the art will appreciate that various other modifications may be made. All these or other variations and modifications are contemplated by the inventors and within the scope of the invention.

What is claimed is:

1. An apparatus comprising:
    an interface mount for attachment to a radiation machine and an accessory to be accepted by the interface mount, wherein
    the interface mount comprises at least one attachment point, the at least one attachment point comprising a housing, an electromagnet operable to generate a magnetic field, and an elongate member received by the electromagnet and supporting the electromagnet, the electromagnet recessed in the housing, and
    the accessory comprises at least one member capable of being held by the magnetic field the accessory including a component configured to shape or modify a property of a beam produced by the radiation machine or the accessory including a device configured for quality control of the radiation machine.

2. The apparatus of claim 1, wherein the at least one member is constructed from a magnetic material.

3. The apparatus of claim 1, wherein the at least one attachment point further comprises a safety lock, the safety lock being configured to hold the accessory accepted by the interface mount.

4. The apparatus of claim 3, wherein the safety lock comprises a latch member and a solenoid operable to move the latch member, the latch member having at least a latched position and an unlatched position.

5. The apparatus of claim 4, wherein the safety lock is configured such that the latch member is disposed at the latched position when the solenoid is unpowered, and at the unlatched position when the solenoid is powered.

6. The apparatus of claim 5, wherein the latch member of the safety lock comprises a ramp configured to allow the at least one member of the accessory to approach to the at least one attachment point by pushing against the ramp while the solenoid is unpowered.

7. The apparatus of claim 5, further comprising at least one switch operable to power to the solenoid, allowing the accessory to be removed from the at least one attachment point.

8. The apparatus of claim 7, wherein the switch is disposed in a handle of the accessory.

9. The apparatus of claim 4, further comprising at least one first sensor at the at least one attachment point of the interface mount, the at least one first sensor configured to detect the latched position or the unlatched position of the latch member.

10. The apparatus of claim 9, further comprising at least one second sensor at the at least one attachment point of the interface mount, the at least one second sensor being configured to detect presence and/or alignment of the accessory.

11. The apparatus of claim 10, wherein the at least one attachment point further comprises a spherical bearing configured to support the electromagnet, the spherical bearing being disposed in the electromagnet and received on the elongate member allowing the electromagnet to tilt, the elongate member comprising an end portion configured to be received in a counterbore in the at least one member of the accessory, the end portion of the elongate member and the counterbore of the at least one member being configured to aid aligning the accessory.

12. The apparatus of claim 11, wherein at least a section of the elongate member is hollow, and the at least one attachment point further comprises a multicolor LED disposed in the elongate member configured to indicate a state of the apparatus.

13. The apparatus of claim 1, wherein the at least one attachment point further comprises a spherical bearing configured to support the electromagnet, the spherical bearing being disposed in the electromagnet and received on the elongate member allowing the electromagnet to tilt.

14. The apparatus of claim 13, wherein the elongate member comprises an end portion configured to be received in a counterbore in the at least one member of the accessory, the end portion of the elongate member and the counterbore of the at least one member being configured to aid aligning the accessory.

15. The apparatus of claim 14, wherein the at least one attachment point of the interface mount further comprises at least one second sensor configured to detect presence or the alignment of the accessory.

16. The apparatus of claim 15, wherein at least a section of the elongate member is hollow, and the at least one attachment point further comprises a multicolor LED disposed in the elongate member configured to indicate a state of the apparatus.

17. The apparatus of claim 16, wherein the at least one member of the accessory comprises a diffuser to diffuse light from the multicolor LED through the counterbore.

18. The apparatus of claim 15, wherein the accessory further comprises at least one pin member adjacent to the at least one member, the at least one pin member being detectable by the at least one second sensor, allowing the at least one second sensor to determine presence or the alignment of the accessory.

19. The apparatus of claim 18, wherein the accessory further comprises an identifier providing a signal indicating identification of the accessory, and the apparatus further comprises a detector configured to detect the signal indicating the identification of the accessory.

* * * * *